(12) United States Patent
Pivetti et al.

(10) Patent No.: US 9,174,937 B2
(45) Date of Patent: Nov. 3, 2015

(54) CRYSTAL FORM OF GLYCOPYRRONIUM CHLORIDE

(75) Inventors: Fausto Pivetti, Parma (IT); Monica Bocchi, Parma (IT); Enrico Vigano, Parma (IT); Ernesto Landonio, Parma (IT)

(73) Assignee: CHIESI FARMACEUTICI S.p.A., Parma (IL)

( * ) Notice: Subject to any disclaimer, the term of this patent is extended or adjusted under 35 U.S.C. 154(b) by 0 days.

(21) Appl. No.: 13/159,922

(22) Filed: Jun. 14, 2011

(65) Prior Publication Data

US 2011/0305645 A1 Dec. 15, 2011

(30) Foreign Application Priority Data

Jun. 14, 2010 (EP) .................................... 10165786

(51) Int. Cl.
  *C07D 207/12* (2006.01)
(52) U.S. Cl.
  CPC .................................. *C07D 207/12* (2013.01)
(58) Field of Classification Search
  CPC .................................................. C07D 207/12
  See application file for complete search history.

(56) References Cited

U.S. PATENT DOCUMENTS

| | | | | |
|---|---|---|---|---|
| 6,307,060 B1 * | 10/2001 | Noe et al. | ....................... | 548/551 |
| 2002/0173536 A1 * | 11/2002 | Noe et al. | ....................... | 514/424 |
| 2007/0185067 A1 * | 8/2007 | Roscher et al. | ................ | 514/174 |
| 2008/0227988 A1 * | 9/2008 | Baxter et al. | .................. | 548/556 |
| 2012/0022127 A1 * | 1/2012 | Allmendinger | ............... | 514/424 |

FOREIGN PATENT DOCUMENTS

| | | |
|---|---|---|
| EP | 1 616 567 | 1/2006 |
| WO | 2008/000482 | 1/2008 |

OTHER PUBLICATIONS

Brittain (Polymorphism in Pharmaceutical Solids, vol. 95, 1999, Taylor & Francis, Harry G. Brittain (Ed.), 427 pp.).*
Morissette et al. (Advanced Drug Delivery Reviews 56 (2004) 275-300).*
Hurst et al., Analytica Chimica Acta, 337 (1997), 233-52.*
Campbell Roberts et al., J. Pharm. Biomed. Anal., 28 (2002) 1149-59.*
Chen et al., J. Pharm. Sci., (1999), v. 88, p. 1191.*
Tiwari et al., J. Pharm. Biomed. Anal., 43 (2007) 865-72.*
Serajuddin, Advanced Drug Delivery Reviews 59 (2007) 603-616.*
Liu, Rong, ed., Water-Insoluble Drug Formulation (CRC Press, 2008) Chapter 15 pp. 417-435.*
Bastin et al., Organic Process Research & Development 2000, 4, 427-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Gould, International J. of Therapeutics 33, 201 (1986).*
Swarbrick et al., eds. Encyclopedia of Pharmaceutical Technology 13 (Marcel Dekker, NY 1996) pp. 453-499.*
Griesser, "Polymorphism in the Pharmaceutical Industry," (2006) Chapter 8 provided.*
U.S. Appl. No. 13/159,872, filed Jun. 14, 2011, Pivetti et al.
European Search Report in Application No. 10165786.4, issued Oct. 7, 2010.
Li et al., Journal of Pharmaceutical Sciences, vol. 86, No. 10, pp. 1073-1078 (1997).
R.K. Khankari et al., "Pharmaceutical Hydrates," Themochimica Acta, vol. 248, pp. 61-79 (1995).
L. Infantes et al., "Extended motifs from water and chemical functional groups in organic molecular crystals," Cryst. Eng. Comm., vol. 5(85), pp. 480-486 (2003).
J. Jacques et al., Enantiomers, Racemates, and Resolutions, John Wiley & Sons, New York, 1981 p. 81.
M.D. Gourlay et al., Crystal Growth & Design, vol. 7, No. 1, pp. 56-63 (2007).
U.S. Appl. No. 14/469,722, filed Aug. 27, 2014, Pivetti et al.

* cited by examiner

*Primary Examiner* — Robert Havlin
(74) *Attorney, Agent, or Firm* — Oblon, McClelland, Maier & Neustadt, L.L.P.

(57) ABSTRACT

A new crystal form of threo glycopyrronium chloride is useful in pharmaceutical applications.

19 Claims, 4 Drawing Sheets

CRYSTAL FORM OF GLYCOPYRRONIUM CHLORIDE

CROSS REFERENCES TO RELATED APPLICATIONS

This application claims priority to European Patent Application No. 10165786.4, filed on Jun. 14, 2010, which is incorporated herein by reference in its entirety.

BACKGROUND OF THE INVENTION

1. Field of the Invention

The present invention relates to a novel crystal form of glycopyrronium chloride. The present invention also relates to methods of preparing such a crystal form and pharmaceutical compositions which contain such a crystal form. The present invention further relates to methods for the treatment of respiratory diseases by administering such a crystal form.

2. Discussion of the Background

Glycopyrronium bromide (also known as glycopyrrolate) is a muscarinic M3 anticholinergic agent used to reduce salivation associated with administration of certain anaesthetics, and as adjunctive therapy for peptic ulcers. It has also been reported to be effective in the treatment of asthmatic symptoms (Hansel et al., Chest, 2005; 128:1974-1979, which is incorporated herein by reference in its entirety). Glycopyrronium bromide is commercially available, and can be synthesized according to the process described in U.S. Pat. No. 2,956,062, which is incorporated herein in its entirety.

Glycopyrronium bromide has two chiral centers corresponding to four isomeric forms comprising 2 pairs of diastereoisomers, namely (3S,2'R)-, (3R,2'S)-, (3R,2'R)-, and (3S,2'S)-[(cyclopentylhydroxyphenylacetyl)oxy]-1,1-dimethylpyrrolidinium bromide. Commercially available glycopyrronium bromide consists of the purified "threo" diastereoisomer (3R,2'S) and (3S,2'R). Different pharmacological properties have been attributed to each of the individual isomers of glycopyrronium bromide.

Glycopyrronium bromide has significant stability problems, especially immediately following a conventional micronization process by milling. It is well known that such milling action may induce the generation of amorphous material that can lead to significant instability which appears to be due to the high hygroscopicity of the amorphous fraction. In WO 2006/100453 (which is incorporated herein by reference in its entirety), other counterions, such as iodide, acetate and sulphate salts, have been mentioned as theoretical alternatives to glycopyrronium bromide for overcoming the milling difficulties associated with the latter. No results in terms of stability have anyway been reported.

US 2002/0173536, which is incorporated herein by reference in its entirety, generically discloses further salts including chloride. However, it has been found that also glycopyrronium chloride is hygroscopic.

In view of these considerations, there is still a need of physical stable crystal forms of glycopyrronium salts.

SUMMARY OF THE INVENTION

Accordingly, it is one object of the present invention to provide novel crystal forms of glycopyrronium chloride.

It is another object of the present invention to provide novel methods for preparing such a crystal form of glycopyrronium chloride.

It is another object of the present invention to provide novel pharmaceutical composition which contain such a crystal form of glycopyrronium chloride.

It is another object of the present invention to provide novel methods of treating certain respiratory diseases by administering such a crystal form of glycopyrronium chloride.

These and other objects, which will become apparent during the following detailed description, have been achieved by the inventors' discovery of a novel crystal form of "threo" diastereoisomer (3R,2'S) and (3S,2'R). glycopyrronium chloride, hereinafter quoted as Form I.

Thus, in a first aspect the present invention provides a novel crystal form of "threo" diastereoisomer (3R,2'S) and (3S, 2'R). glycopyrronium chloride, hereinafter quoted as Form I.

Said form is a thermodynamically stable pseudopolymorph, i.e. the monohydrate.

Form I may be produced by crystallization from appropriate solvents and conditions and it is distinguishable, inter alia, by its characteristic peaks in the X-ray powder diffraction (XRPD) pattern.

Accordingly, in a second aspect, the present invention provides methods for the preparation of said crystal form.

In a third aspect, the present invention provides pharmaceutical compositions comprising glycopyrronium chloride Form I, and, optionally, one or more pharmaceutically acceptable excipients.

In a fourth aspect, the present invention provides glycopyrronium chloride Form I for use as a medicament.

In a fifth aspect the present invention provides glycopyrronium chloride Form I for use for the prevention or treatment of a disease selected from the group consisting of COPD (chronic bronchitis and emphysema); asthma; acute lung injury (ALI); cystic fibrosis; rhinitis; adult or respiratory distress syndrome (ARDS); urinary incontinence; irritable bowel syndrome; psoriasis; hyperhydrosis; sialorrhea; and gastrointestinal ulcers. In a sixth aspect the invention provides the use of glycopyrronium chloride Form I in the preparation of a medicament for the prevention or treatment of a disease selected from the group consisting of COPD (chronic bronchitis and emphysema); asthma; acute lung injury (ALI); cystic fibrosis; rhinitis; adult or respiratory distress syndrome (ARDS); urinary incontinence; irritable bowel syndrome; psoriasis; hyperhydrosis; sialorrhea; and gastrointestinal ulcers.

In a further aspect the present invention provides method for the prophylaxis or treatment of a disease selected from the group consisting of COPD (chronic bronchitis and emphysema); asthma; acute lung injury (ALI); cystic fibrosis; rhinitis; adult or respiratory distress syndrome (ARDS); urinary incontinence; irritable bowel syndrome; psoriasis; hyperhydrosis; sialorrhea; and gastrointestinal ulcers, said method comprising the administration of a therapeutical effective amount of glycopyrronium chloride Form I.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Unless defined otherwise, all technical and scientific terms used herein have the same meaning as is commonly understood in the art to which this subject matter belongs.

The term "threo glycopyrronium chloride" indicates the mixture of the diastereoisomer (3R,2'S) and (3S,2'R) of [(cyclopentylhydroxyphenylacetyl)oxy]-1,1-dimethylpyrrolidinium chloride. The ratio between the two diastereoisomers may vary between 40:60 and 60:40, and it is preferably 50:50.

The diastereoisomeric ratio can be determined by methods familiar to those skilled in the art, such as HPLC, and NMR spectroscopy.

The term "amorphous" describes a non-ordered solid state characterized by a diffused X-ray powder diffraction with no sharp peaks.

The term "pseudopolymorph" refers to a hydrate of a compound. In other words it is a crystal form that incorporates a stoichiometric amount of water.

"An effective amount of a compound for treating a particular disease" is an amount that is sufficient to ameliorate, or in some manner reduce the symptoms associated with the disease.

The term "thermodynamically stable" refers to a crystal form that, during storage under long term conditions (25° C., 60% relative humidity) does not convert into another one for a pharmaceutically acceptable period of time (at least 3 months, preferably 6 months, more preferably 1 year).

The term "high level of chemical purity" refers to a crystal form wherein the total amount of readily detectable impurities as determined by standard methods of analysis, such as thin layer chromatography (TLC) or high performance liquid chromatography (HPLC), used by those of skill in the art to assess such purity, is less than 5%, advantageously less than 2.5%, preferably less than 1.0, more preferably less than 0.5% w/w.

The term "high level of crystallinity" refers to a crystal form wherein the percentage of crystallinity is equal to or higher than 90%, preferably higher than 95% w/w as determined by standard methods of analysis used by those of skill in the art, such as X-ray powder diffraction or microcalorimetry.

The present inventors have observed that threo glycopyrronium chloride in the solid state is a hygroscopic material.

Therefore, the present invention provides a thermodynamically stable crystalline form of threo glycopyrronium chloride, quoted hereinafter as Form I, having a significant less tendency of adsorbing water.

Said form is a pseudopolymorph. X-ray diffraction on single crystal has indeed demonstrated that it corresponds to the monohydrate form. The water percentage determined by Karl-Fischer method, is also compatible with the monohydrate form, as it turned out to be 5.3% w/w±0.1 (theoretical value 4.8%). Crystal form I may be characterized in a variety of ways.

Figure 1:
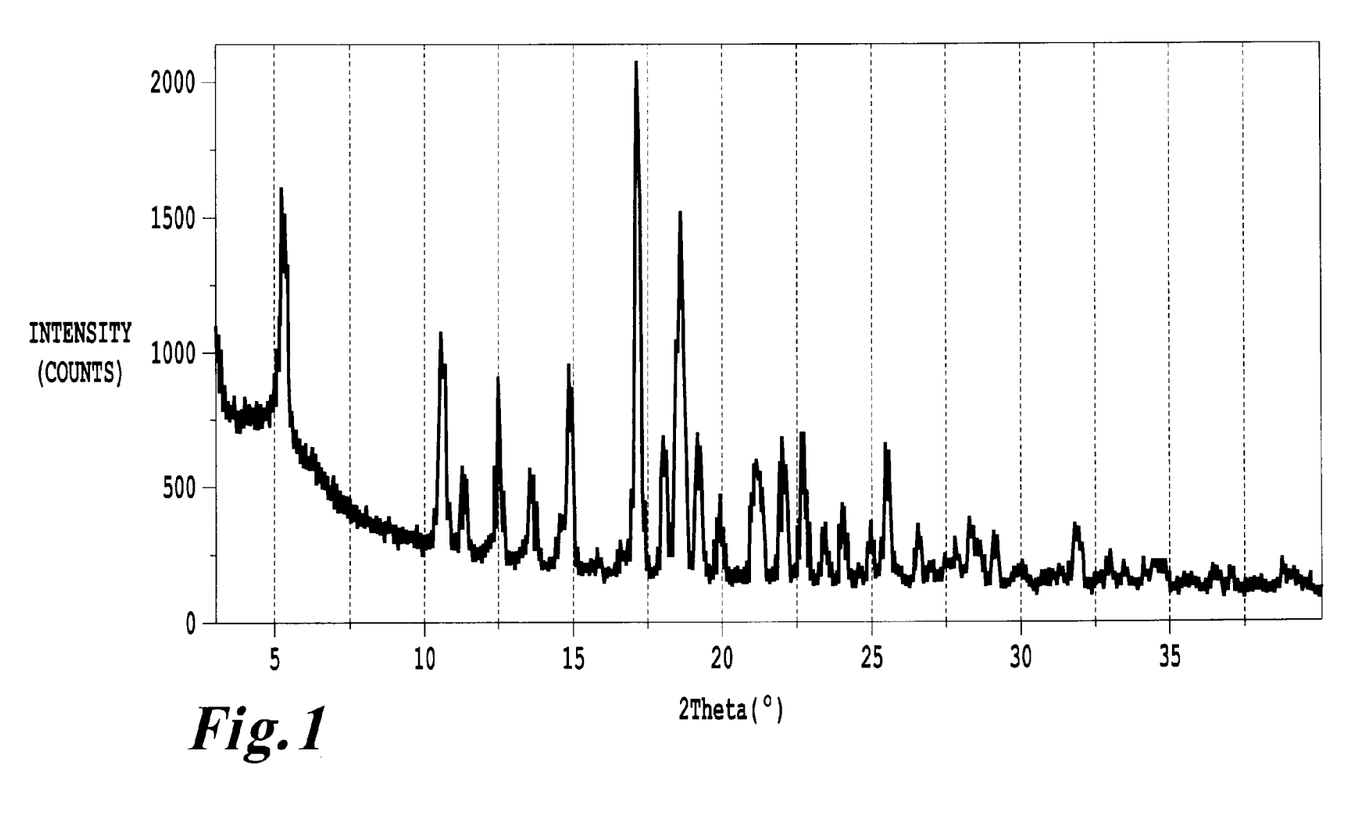
FIG. 1 is an X-ray powder diffraction (XRPD) pattern of crystal Form 1.

Its thermal trace, shown in FIG. 1, exhibits a first endothermic peak starting with an onset at about 99° C. with the melting peak at about 117° C., corresponding to the loss of water, and a second endothermic peak having an onset at about 164° C. with the melting peak at about 190° C.

In one embodiment, Form I has the characteristic diffraction peaks expressed in angle 2-theta at approximately the values reported in Table 1, using Cu-Kα radiation.

TABLE 1

| Diffraction Angle (°2θ) |
|---|
| 5.40 |
| 10.65 |
| 14.88 |
| 17.16 |
| 18.47 |
| 18.69 |

When used with reference to X-ray powder diffraction (XRPD) peaks, the term "approximately" means that there is an uncertainty in the measurements of the angle 2-theta of ±0.2° (expressed in degrees 2-theta).

In another embodiment, Form I has the characteristic diffraction peaks expressed in angle 2-theta at approximately the values reported in Table 2, using Cu-Kα radiation.

TABLE 2

| Diffraction Angle (°2θ) |
|---|
| 5.40 |
| 10.65 |
| 12.46 |
| 14.88 |
| 17.16 |
| 18.47 |
| 18.69 |

In another embodiment, Form I has the characteristic diffraction peaks expressed in angle 2-theta at approximately the values reported in Table 3, using Cu-Kα radiation.

TABLE 3

| Diffraction Angle (°2θ) |
|---|
| 5.40 |
| 10.65 |
| 12.46 |
| 14.88 |
| 17.16 |
| 18.47 |
| 18.69 |
| 19.24 |

In another embodiment, Form I has the characteristic diffraction peaks expressed in angle 2-theta at approximately the values reported in Table 4, using Cu-Kα radiation.

TABLE 4

| Diffraction Angle (°2θ) |
|---|
| 5.40 |
| 10.65 |
| 11.32 |
| 12.46 |
| 14.88 |
| 17.16 |
| 18.47 |
| 18.69 |
| 19.24 |
| 22.08 |
| 22.74 |
| 25.40 |
| 25.54 |
| 26.57 |
| 28.40 |

In another embodiment, the Form I is characterized by an XRPD pattern comprising characteristic peaks with approximate 2θ values as indicated in Table 1, and with relative intensities deviating by no more than ±30%, preferably no more than ±10% from the values given in Table 2. The relative intensity is the ratio of the peak intensity to that of the most intense peak.

TABLE 2

| Diffraction Angle (°2θ) | Relative Intensity (%) |
|---|---|
| 5.40 | 69.3 |
| 10.65 | 86.7 |
| 11.32 | 14.4 |
| 12.31 | 16.2 |
| 12.46 | 33.7 |
| 13.61 | 11.1 |
| 14.49 | 13.0 |
| 14.88 | 41.2 |
| 17.16 | 100.0 |
| 18.09 | 28.3 |
| 18.47 | 50.7 |
| 18.69 | 44.6 |
| 19.13 | 22.5 |
| 19.24 | 27.9 |
| 21.12 | 24.2 |
| 21.30 | 21.1 |
| 22.08 | 27.3 |
| 22.74 | 23.6 |
| 23.46 | 14.0 |
| 25.40 | 16.8 |
| 25.54 | 21.8 |
| 26.57 | 13.1 |
| 28.40 | 9.5 |

Crystal Form I may also be characterized by its FT-IR spectrum. The FT-IR spectrum, shown in FIG. 3, exhibits the main bands at the following approximate values (intensity between brackets): 3457 cm$^{-1}$ (m), 3369 (m), 1728 (s), 1414 (s), 1380 (s), 1172 (vs), 695 (vs). Legend: m=medium, s=strong, vs=very strong. The accuracy is ±1 cm$^{-1}$.

Crystal Form I of threo glycopyrronium chloride is characterized by a high level of chemical purity and crystallinity as well as good handling characteristics, in particular for the preparation of pharmaceutical compositions in the solid state. In fact, being a monohydrate, crystal Form I has water incorporated in its unit crystal cell, and hence tends to absorb less moisture from the environment. Moreover upon milling, as demonstrated in the following Example, ground crystal Form I shows an overlapping XRPD pattern, thus indicating that the degree of crystallinity is substantially unchanged.

The present invention also provides a process for the preparation of said crystal form comprising the crystallization of threo glycopyrronium chloride from a solution thereof in a solvent or a mixture of solvents under conditions which yield crystal Form I. The precise conditions under which said Form is obtained may be empirically determined and it is only possible to give a number of methods which have been found to be suitable in practice.

In general, the crystal Form I of the invention may be prepared by crystallization under particular conditions of threo glycopyrronium chloride or by re-crystallization of any other crystal forms which may become known in the future.

Thus, for example, crystal Form I may be prepared by crystallization at room temperature of threo glycopyrronium chloride from a solution thereof in a chlorinated solvent such as chloroform and dichloromethane. Otherwise, it may be prepared by crystallization at room temperature from aqueous or methanol solutions or from 1:1 v/v mixtures of water and acetonitrile or water and ethanol.

The crystal form of the invention is readily isolable and may be filtered off from the crystallization medium, optionally after washing and drying.

If desired, the obtained crystal form prepared as above may further be re-crystallized using conditions similar to those previously described. For subsequent crystallizations, it may be preferable to add "seeds" of the crystalline material to the solution in order to induce crystallization.

Threo glycopyrronium chloride, in turn, can be prepared according to the methods disclosed in the co-filed patent application (European Patent Application No. 10165784.9, filed on Jun. 14, 2010, the disclosure of which is incorporated herein by reference in its entirety. Specific reference is made to pages 4, line 2 to page 7, line 21 and to the Examples of said application.

In particular, for larger-scale synthesis, threo glycopyrronium chloride can be prepared starting from commercially available threo glycopyrronium bromide and applying ion exchange technology according to the following procedure.

A column of anion exchange resin is prepared and activated by treatment with, for example, a NaCl solution, then loaded with threo glycopyrronium bromide. The anion exchange occurs on the column when glycopyrronium bromide is allowed to flow through the column: bromide ions are withdrawn by the resin and exchanged with chloride ions as counterions of glycopyrronium. Threo glycopyrronium chloride is then eluted from the column with an appropriate solvent or solvent mixture, such as ethanol or an ethanol/water mixture.

Suitable ion exchange resins are commercially available. They include strong anion exchange resins like Amberlite® IRA900 or FAP90. The amount of resin should be adjusted on the basis of the amount of glycopyrronium bromide to be loaded and of the exchange capacity of the resin itself, as number of chloride equivalents per kg or liter of resin. Suitable excesses of resin chloride equivalents, generally 2 to 5 equivalents versus bromide equivalents to be loaded, are generally considered appropriate in order to get low bromide residue.

Resins are preferably loaded in glass columns of suitable diameter and length. If not already activated as chloride anion exchange, resins can be activated by contacting with an aqueous solution of sodium chloride, generally 5 to 10% p/v; elution with water follows to remove excess sodium chloride and finally the column is conditioned with the solvent to be used in glycopyrronium elution.

Glycopyrronium bromide is dissolved in appropriate volumes of a suitable solvent and the solution is loaded at the top of the resin column. Then eluting solvent is applied to the column: elution can occur by gravitation or through the use of a pump: in case of gravitation, flow is regulated through the height of the solvent reservoir; in case of pumping, flow is regulated by the pump speed. Solvent flow rate should be regulated on the basis of the bed volume in order to allow sufficient residence time of glycopyrronium within the column.

Threo glycopyrronium chloride solution is collected at the exit of the column: several fractions are collected of suitable volume, depending on the column bed volume. After analytical checks (e.g. by TLC), suitable fractions are blended for the following work-up and isolation.

The pooled fractions may be decolored (e.g. with charcoal). They can be filtered, for instance through mineral filters such as Dicalite®. The pooled fractions can be concentrated by evaporation, for example through use of a rotary evaporator.

The crystal Form I of threo glycopyrronium chloride may be formulated for administration in any convenient way and hence the invention provides pharmaceutical compositions thereof. Pharmaceutical compositions can be prepared by admixture of Form I of threo glycopyrronium chloride and one or more pharmaceutically acceptable excipients. Depending on the nature of the medical disease or condition to be treated, and the type of patient, the pharmaceutical compositions may be formulated to be delivered by any suitable route, including oral, intravenous, parenteral, inhalation, intranasal, topical, subcutaneous, intramuscular, rectal, vaginal. Suitable dosage forms include conventional forms such as tablets, capsules, powders, sustained release formulations, ointments, gels, creams, suppositories, eye drops, transdermal patches, syrups, solutions, suspensions, aerosols, solutions for nebulizers, nasal sprays, etc.

Suitable excipients include carriers, diluents, wetting agents, emulsifying agents, binders, coatings, fillers, glidants, lubricants, disintegrants, preservatives, surfactants, pH buffering substances and the like. Examples of excipients and their use are provided in the *Handbook of Pharmaceutical Excipients*, 5$^{th}$ ed. (2006), Ed. Rowe et al., Pharmaceutical Press, which is incorporated herein by reference in its entirety.

In a preferred embodiment, the composition is formulated for delivery by the inhalation or intranasal routes, for instance as a propellant containing solution or suspension for aerosol, as a dry powder for inhalation, or as a nasal spray. Even more preferably, the composition is formulated as dry powder for inhalation to the lungs.

The above pharmaceutical compositions for delivery by inhalation may be filled in suitable devices such as pressurized metered dose inhalers (pMDIs) or dry powder inhalers (DPIs).

The compositions may also comprise, if required, one or more other therapeutic agents, preferably those currently used in the treatment of respiratory disorders, e.g. corticosteroids, beta$_2$-agonists, and phosphodiesterase-4 (PDE-4) inhibitors.

Suitable dosages of Form I of threo glycopyrronium chloride in the pharmaceutical compositions of the invention may easily be established by the attending physician and will depend on the type of patient and nature of the decision condition, and on the mode of drug delivery. Dosage levels of the order of about 0.1 μg to about 25 mg per kilogram of body weight per day may be useful. For prevention or treatment of respiratory conditions crystal Form I is likely to be delivered by inhalation, in which case the preferred dosage is probably about 0.5 to 100 μg per inhalation device actuation, preferably about 1 to 40 μg per actuation, and more preferably about 5 to 26 μg per actuation.

The crystal Form I of the invention may be used for prophylactic purposes or for symptomatic relief for a wide range of conditions including: respiratory disorders such as chronic obstructive pulmonary disease (COPD) and asthma of all types. Other respiratory disorders for which the product of the invention may be beneficial are those characterized by obstruction of the peripheral airways as a result of inflammation and presence of mucus, such as chronic obstructive bronchiolitis, chronic bronchitis, emphysema, acute lung injury (ALI), cystic fibrosis, rhinitis, and adult or respiratory distress syndrome (ARDS).

In addition, the crystal Form I of the invention may be useful in treating smooth muscle disorders such as urinary incontinence and irritable bowel syndrome; skin diseases such as psoriasis; hyperhydrosis and sialorrhea; and gastrointestinal ulcers.

Other features of the invention will become apparent in the course of the following descriptions of exemplary embodiments which are given for illustration of the invention and are not intended to be limiting thereof.

EXAMPLES

Example 1

Preparation of Crystal Form I of Threo Glycopyrronium Chloride

Resin Amberlite® IRA900 Cl (500 g) was suspended in 1500 ml of a mixture of ethanol/water 50/50 v/v and loaded in a glass column of 60 mm internal diameter with bottom filter and valve. The excess solvent was allowed to pass through the column: the bed height was about 25 cm, corresponding to a bed volume of 700 ml. Threo glycopyrronium bromide (74 g, 0.186 mol) was dissolved in 280 ml of a mixture of ethanol/water 50/50 v/v and loaded at the top of the column. The solution was passed through the column followed by a mixture of ethanol/water 50/50 v/v as eluting solvent. Elution occurred by gravitation and the flow rate was adjusted to 15 to 20 ml/min; 80 to 100 ml fractions were collected at the bottom of the column and analyzed for glycopyrronium content (by TLC as from pharmacopeia): glycopyrronium started eluting in fraction 3, its concentration was at a maximum in fractions 5 to 8 and then decreased until it disappeared in fraction 17. Fractions 3 to 16 were blended and the resulting solution (1.4 l) was decolored with charcoal, filtered through a Dicalite® layer and concentrated in a rotary evaporator.

The oily residue was suspended in ethyl acetate (740 ml) and concentrated again in order to remove water as azeotrope; after partial concentration and addition of fresh ethyl acetate, threo glycopyrronium chloride crystallized as a white powder. The suspension was stirred and cooled at 0° C., and the solid was filtered and dried under vacuum at 50° C. Threo glycopyrronium chloride (65.0 g, 0.175 mol) was obtained as the monohydrate crystal, with 94% yield. The obtained product was characterized as having more than 99% purity.

Example 2

Characterization in the Solid State of Crystal Form I of Threo Glycopyrronium Chloride Crystal Form I of threo glycopyrronium chloride was analyzed in the solid state by X-ray powder diffraction (XRPD), IR spectroscopy and differential scanning calorimetry.

1. X-Ray Powder Diffraction (XRPD)

The XRPD analyses were carried out on a PANanalytical X'pert Pro X-ray powder diffractometer using Cu Kα radiation. The instrument is equipped with a X'Celerator detector. A theta-two theta continuous scan from 2.5 degrees 2-theta to 45 degrees 2-theta was used. The sample was prepared for analysis by placing it in a quartz sample holder. The XPRD pattern is shown in FIG. 1.

2. IR Spectrum

Figure 2:
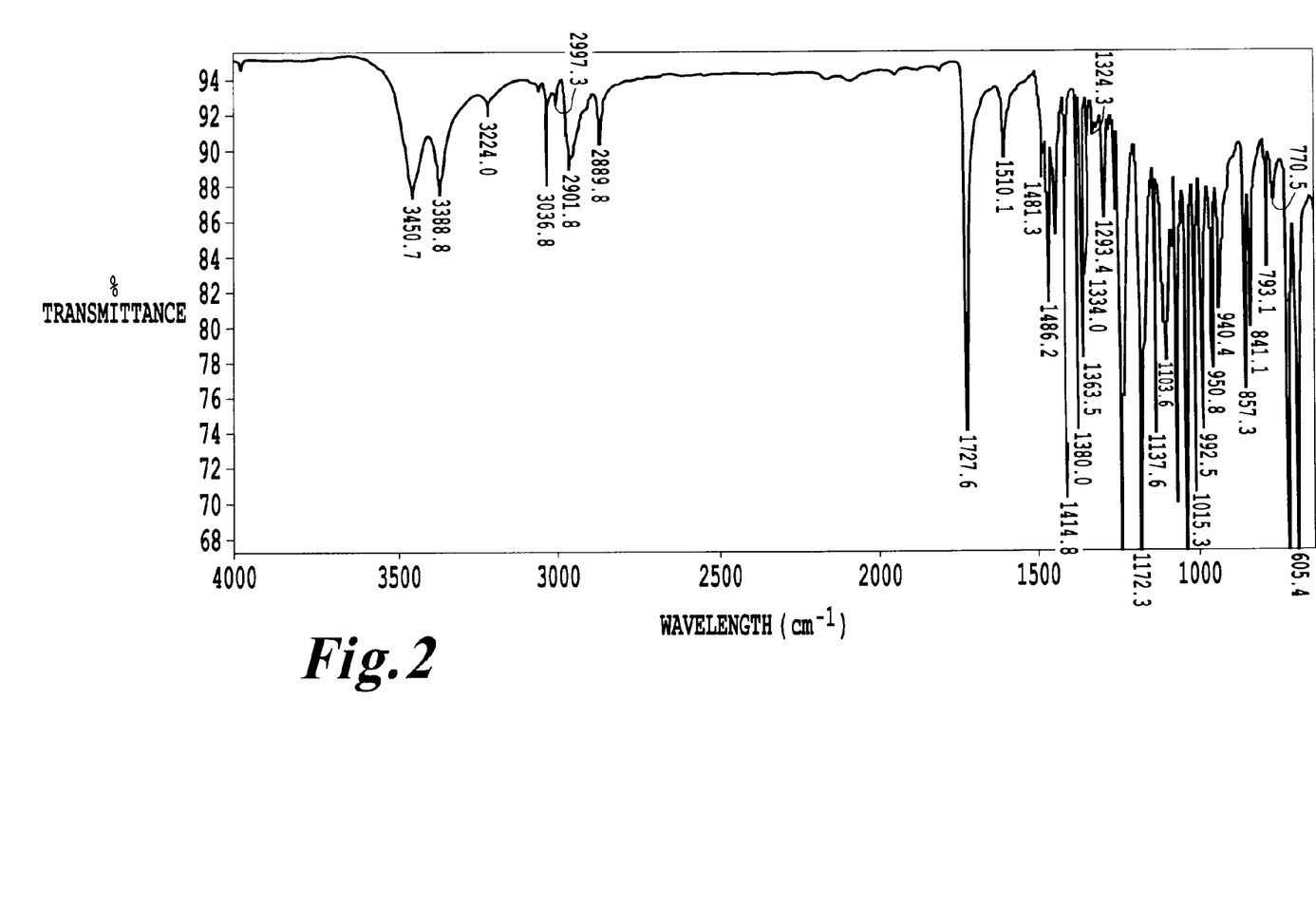
FIG. 2 is an IR spectrum of crystal Form I.

The IR spectra was acquired on a Nicolet FT-IR 6700 ThermoFischer spectrophotometer. The sample was prepared as a KBr disk. The spectrum which was scanned in the range 6400 to 200 cm$^{-1}$, is shown in FIG. 2.

3. Differential Scanning Calorimetry (DSC)

Figure 3:
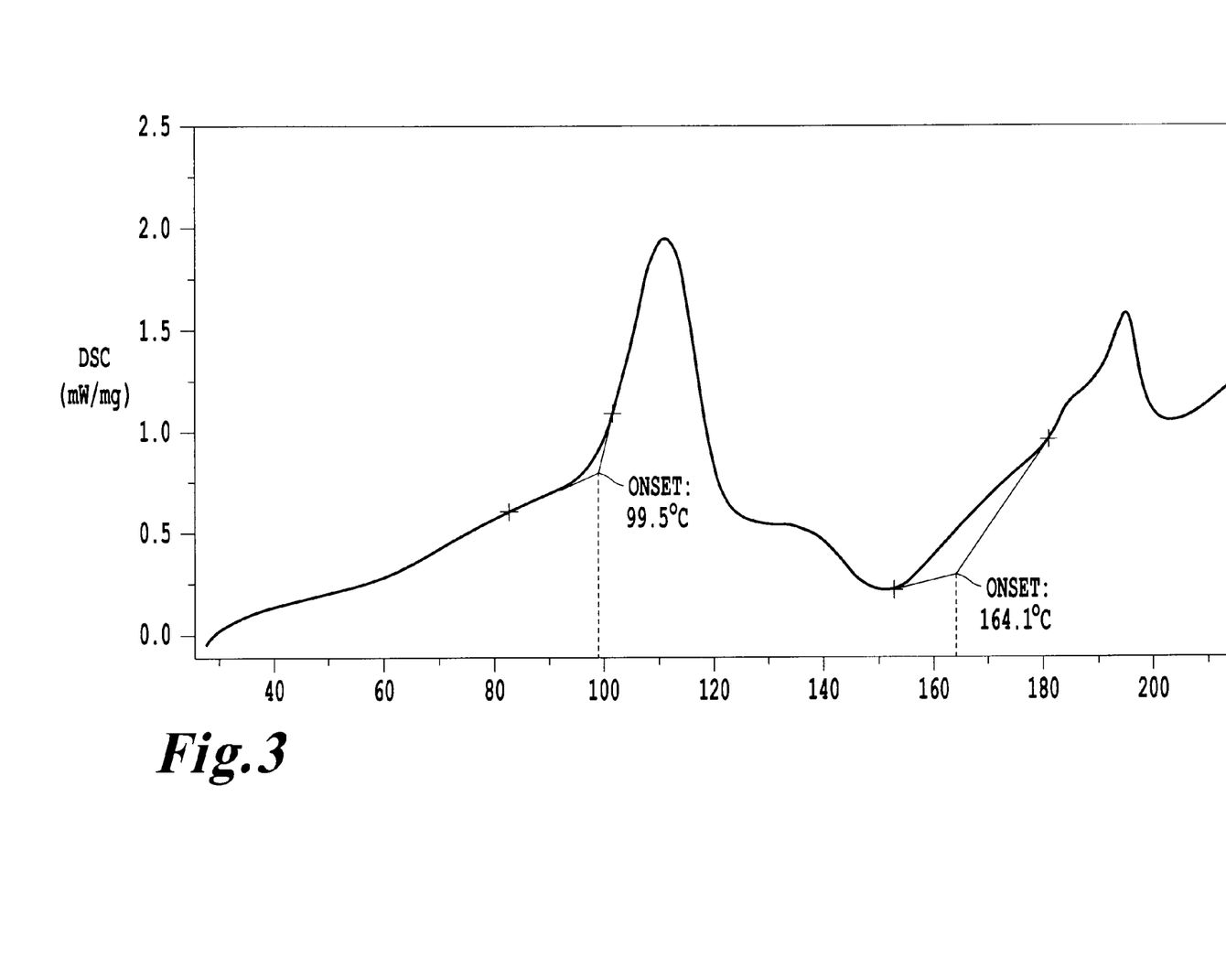
FIG. 3 is a differential scanning calorimetry (DSC) thermal trace of crystal Form I.

The differential scanning calorimetry data were obtained on a STA 409 Luxx® Netzsch instrument. Approximately 2 to 5 mg of the sample was placed into a DSC pan, and the weight was accurately measured and recorded. The pan was hermetically sealed. The sample was heated under nitrogen at a rate of 10° C./min, from 25° C. to a final temperature of 220° C. The thermogram is shown in FIG. 3.

Example 3

Investigation of the Effect of Milling

Figure 4:
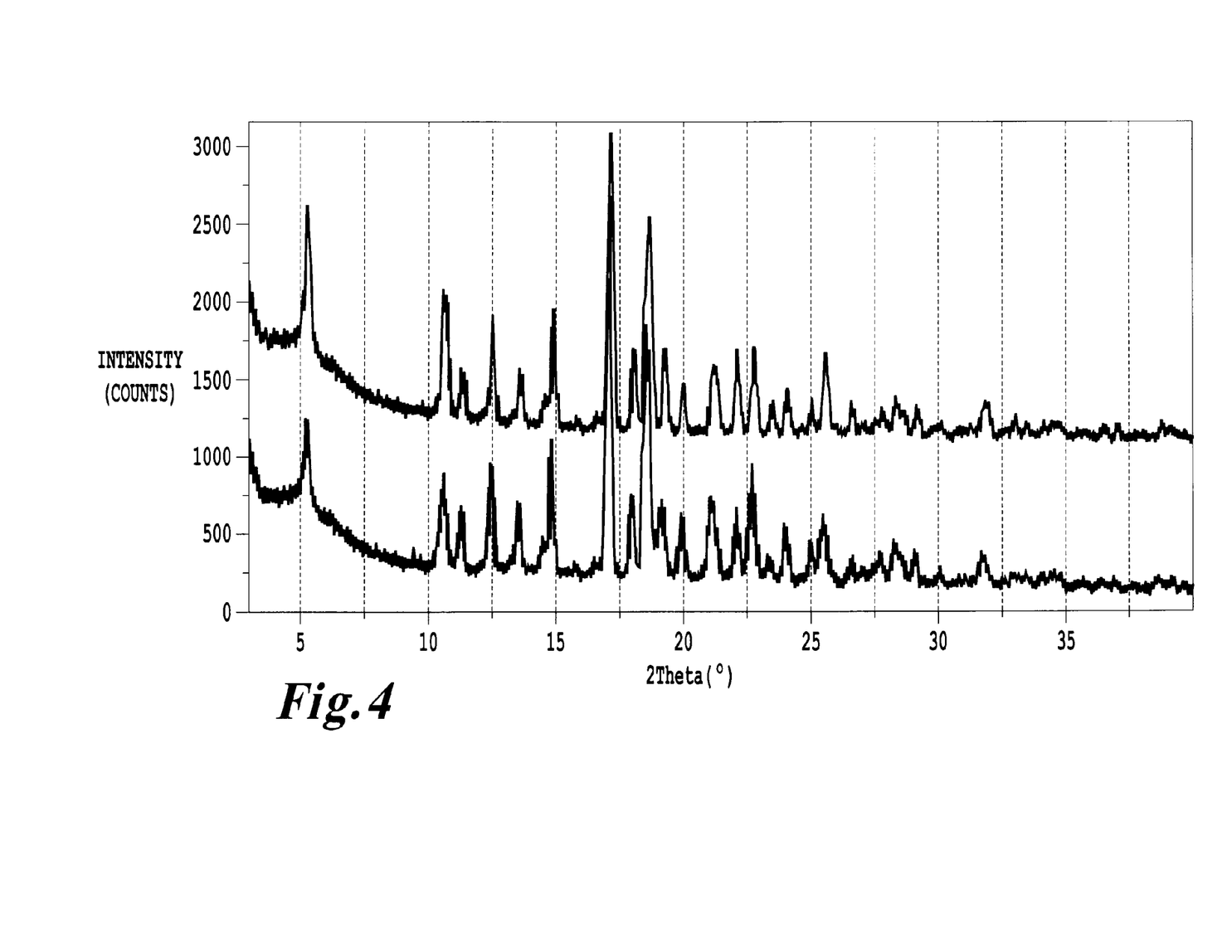
FIG. 4 is an XRPD comparison between crystal Form I ground sample and reference crystal Form I.

A sample of crystal Form I as obtained in Example 1 was ground by ball milling in a Retsch MM 200 grinder at a frequency of 30 Hz. It was then analyzed to determine its diffraction pattern. The stability of the ground sample was determined by comparing its diffraction pattern with that of the standard reference pattern. The ground sample showed an overlappable XRPD pattern (see FIG. 4), indicating the degree of crystallinity is substantially unchanged.

Example 4

Single Crystal Analysis

A sample of Form I of threo glycopyrrolate chloride was recrystallized and submitted for single crystal analysis. The crystals were prepared by dissolving 0.050 g of solid in 4 mL of Dichloromethane. The solution was heated until boiling point, filtered and left to evaporate.

Data Collection and Analysis.

A colorless needle of threo glycopyrronium chloride FORM I having approximate dimensions of 0.4×0.2×0.02 mm, was mounted on a glass fiber in random orientation. Crystal data were collected at room temperature on a X-ray Diffractometer Oxford Xcalibur S Mo-K radiation, $\lambda$=0.71073 Å with Monochromator graphite and Sapphire CCD detector. Cell constants and an orientation matrix for data collection were obtained from least-square refinement using the setting angles of 25 reflections in the range 7°<θ<15°. The space group, determined by the program XPREP, was P21/c. The structure was solved by direct methods and refined by full-matrix least-squares on $F^2$ with SHELX97 program package.

A calculated XRPD pattern was generated for Cu radiation using Mercury v 2.2 and the atomic coordinates, space group, and unit cell parameter from the single crystal data. The crystal data and structure refinement are reported in Table 3.

TABLE 3

| | |
|---|---|
| Empirical formula | C19 H30 Cl N O4 |
| Formula weight | 371.89 |
| Temperature | 293(2)K |
| Wavelength | 0.71073 Å |
| Crystal system | Monoclinic |
| Space group | P21/c |
| Unit cell dimensions | a = 17.4163(6) Å   $\alpha$ = 90°. |
| | b = 8.9340(2) Å   $\beta$ 104.782(3)°. |
| | c = 13.5563(4) Å   $\gamma$ = 90°. |
| Volume | 2039.51(10) Å$^3$ |
| Z | 4 |
| Density (calculated) | 1.211 Mg/m$^3$ |
| Absorption coefficient | 0.209 mm$^{-1}$ |
| F(000) | 800 |
| Crystal size | 0.8 × 0.6 × 0.1 mm$^3$ |
| Theta range for data collection | 2.85 to 29.12° |
| Index ranges | −23 <= h <= 19, −11 <= k <= 11, −15 <= l <= 18 |
| Reflections collected | 15215 |
| Independent reflections | 4796 [R (int) = 0.0235] |
| Completeness to theta = 25.00° | 99.9% |
| Absorption collection | Semi-empirical from equivalents |
| Max. and min. transmission | 1.00000 and 0.98773 |
| Refinement method | Full-matrix least-squares on $F^2$ |
| Data/restraints/parameters | 4796/0/238 |

TABLE 3-continued

| | |
|---|---|
| Goodness-of-fit on $F^2$ | 0.961 |
| Final R indices [1 > 2sigma(I)] | R1 = 0.0582, wR2 = 0.1566 |
| R indices (all data) | R1 = 0.0990, wR2 = 0.1752 |
| Largest diff. peak and hole | 0.317 and −0.279 e.Å$^{-3}$ |

The structure is characterized by four molecules of glycopyrronium chloride and four molecules of water in the unit cell. The analysis on the powder sample (Form I) and the data obtained by X-ray diffraction on single crystal confirm the identity of the crystal form.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. Crystalline threo glycopyrronium chloride-monohydrate, consisting of (3R,2'S)- and (3S,2'R)-[(cyclopentylhydroxyphenylacetyl)oxy]-1,1-dimethylpyrrolidinium chloride monohydrate, having XRPD peaks using Cu-Kα radiation at 2θ degrees (±0.2°) of 5.40, 10.65, 14.88, 17.16, 18.47, and 18.69.

2. Crystalline threo glycopyrronium chloride monhydrate according to claim 1, having XRPD peaks using Cu-Kα radiation at 2θ degrees (±0.2°) of 5.40, 10.65, 12.46, 14.88, 17.16, 18.47, and 18.69.

3. Crystalline threo glycopyrronium chloride monhydrate according to claim 1, having XRPD peaks using Cu-Kα radiation at 2θ degrees (±0.2°) of 5.40, 10.65, 12.46, 14.88, 17.16, 18.47, 18.69, and 19.24.

4. Crystalline threo glycopyrronium chloride monhydrate according to claim 1, having XRPD peaks using Cu-Kα radiation at 2θ degrees (±0.2°) of 5.40, 10.65, 11.32, 12.46, 14.88, 17.16, 18.47, 18.69, 19.24, 22.08, 22.74, 25.40, 25.54, 26.57, and 28.40.

5. Crystalline threo glycopyrronium chloride monhydrate according to claim 1 having peaks in its IR spectrum (±1 cm$^{-1}$) at 3457 cm$^{-1}$, 3369 cm$^{-1}$, 1728 cm$^{-1}$, 1414 cm$^{-1}$, 1380 cm$^{-1}$, 1172 cm$^{-1}$, and 695 cm$^{-1}$.

6. A process for preparing crystalline threo glycopyrronium chloride monhydrate according to claim 1, which comprises crystallizing threo glycopyrronium chloride at room temperature from a solution thereof in an aqueous or methanol solution or from a 1:1 v/v mixture of water and acetonitrile or water and ethanol.

7. A process for preparing crystalline threo glycopyrronium chloride monhydrate according to claim 2, which comprises crystallizing threo glycopyrronium chloride at room temperature from a solution thereof in an aqueous or methanol solution or from a 1:1 v/v mixture of water and acetonitrile or water and ethanol.

8. A pharmaceutical composition, comprising crystalline threo glycopyrronium chloride monhydrate according to claim 1 and at least one pharmaceutically acceptable excipient.

9. A pharmaceutical composition according to claim 8, further comprising another therapeutic agent.

10. A pharmaceutical composition according to claim 8, further comprising a therapeutic agent selected from the group consisting of a corticosteroid, a beta$_2$-agonist, and a phosphodiesterase-4 (PDE-4) inhibitor.

11. A pharmaceutical composition according to claim 8, which is in the form of an inhalable aerosol comprising a propellant.

12. A pharmaceutical composition according to claim 8, which is in the form of an inhalable dry powder.

13. A pharmaceutical composition, comprising crystalline threo glycopyrronium chloride monohydrate according to claim 5 and at least one pharmaceutically acceptable excipient.

14. A pharmaceutical composition according to claim 13, further comprising another therapeutic agent.

15. A pharmaceutical composition according to claim 13, further comprising a therapeutic agent selected from the group consisting of a corticosteroid, a beta$_2$-agonist, and a phosphodiesterase-4 (PDE-4) inhibitor.

16. A pharmaceutical composition according to claim 13, which is in the form of an inhalable aerosol comprising a propellant.

17. A pharmaceutical composition according to claim 13, which is in the form of an inhalable dry powder.

18. A method for the prevention or treatment of a disease selected from the group consisting of chronic bronchitis, emphysema, asthma, acute lung injury, cystic fibrosis, rhinitis, adult respiratory distress syndrome, urinary incontinence, irritable bowel syndrome, psoriasis, hyperhydrosis, sialorrhea, and gastrointestinal ulcer, said method comprising administering to a subject in need thereof an effective amount of crystalline glycopyrronium chloride monohydrate according to claim 1.

19. A method for the prevention or treatment of a disease selected from the group consisting of chronic bronchitis, emphysema, asthma, acute lung injury, cystic fibrosis, rhinitis, adult respiratory distress syndrome, urinary incontinence, irritable bowel syndrome, psoriasis, hyperhydrosis, sialorrhea, and gastrointestinal ulcer, said method comprising administering to a subject in need thereof an effective amount of crystalline glycopyrronium chloride monohydrate according to claim 5.

* * * * *